(12) United States Patent
Sayer et al.

(10) Patent No.: US 8,871,683 B2
(45) Date of Patent: Oct. 28, 2014

(54) DICAMBA HERBICIDE COMPOSITION

(75) Inventors: Chad Richard Ord Sayer, Brighton (AU); Graeme Sutton, Ashwood (AU); Aristos Panayi, Taylors Hill (AU)

(73) Assignee: Nufarm Australia Limited, Laverton North (AU)

( * ) Notice: Subject to any disclaimer, the term of this patent is extended or adjusted under 35 U.S.C. 154(b) by 391 days.

(21) Appl. No.: 12/821,509

(22) Filed: Jun. 23, 2010

(65) Prior Publication Data

US 2010/0331188 A1    Dec. 30, 2010

Related U.S. Application Data

(63) Continuation-in-part of application No. PCT/AU2009/001690, filed on Dec. 23, 2009.

(30) Foreign Application Priority Data

Dec. 23, 2008   (AU) ................................ 2008906606

(51) Int. Cl.
*A01N 37/36*   (2006.01)
*A01N 37/10*   (2006.01)
*A01N 37/40*   (2006.01)
*A01N 39/04*   (2006.01)

(52) U.S. Cl.
CPC ................ *A01N 37/40* (2013.01); *A01N 39/04* (2013.01)
USPC ............................ 504/324; 504/144; 514/159

(58) Field of Classification Search
USPC .................................. 514/159; 504/324, 144
See application file for complete search history.

(56) References Cited

U.S. PATENT DOCUMENTS

2008/0032892 A1    2/2008   Linton

FOREIGN PATENT DOCUMENTS

| EP | 0512738 B1 | 1/1997 |
|----|------------|--------|
| GB | 851084 A   | 10/1960 |
| GB | 1339315 A  | 12/1973 |

OTHER PUBLICATIONS

Lawn Weed Killer (Retrieved on Jan. 22, 2010); http://www.lillymiller.com/labels/LillyMiller/09606340.pdf>published on May 8, 2007 as per Wayback Engine. 4 pages.
International Search Report PCT/AU2009/001690.

*Primary Examiner* — John Pak
*Assistant Examiner* — Nathan W Schlientz

(57) ABSTRACT

A herbicidal composition comprising dicamba in each of the monomethylamine and dimethylamine salts wherein the ratio of monomethylamine:dimethylamine is from 20:1 to 1:1.

17 Claims, 1 Drawing Sheet

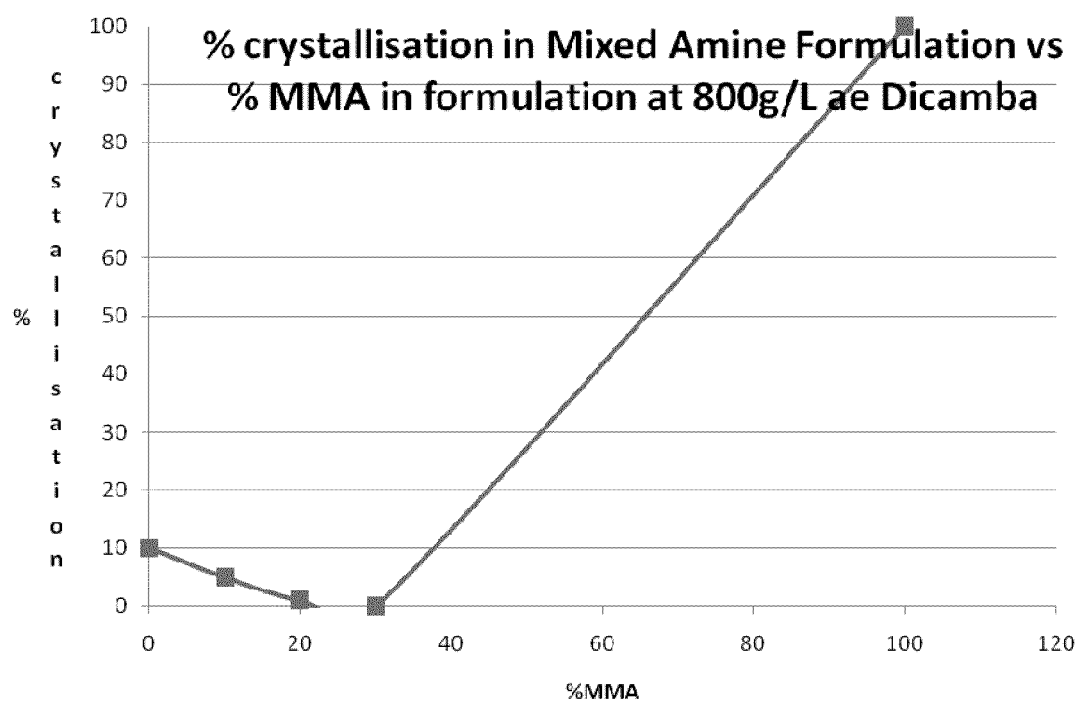

DICAMBA HERBICIDE COMPOSITION

The present application is a divisional application from International PCT patent application number PCT/AU2009/001690, the entire disclosure of which is incorporated herein by reference.

FIELD

This invention relates to a dicamba herbicide composition which allows a high loading of dicamba herbicide to be provided in aqueous composition. The invention also relates to an aqueous composition having a high loading of dicamba and the preparation of the salt composition and high loading aqueous composition and methods of controlling plant growth using the compositions.

BACKGROUND

Auxin herbicides have been widely used as herbicides and include phenoxyacids such as phenoxy-acetic, -propionic and -butyric acid herbicides and their esters; phenyl acid herbicides such as 3,6-dichloro-o-anisic acid (dicamba); pyridyloxy acids such as 3,5,6,pyridyloxy acetic acid; and pyridine carboxylic acids such as 3,6-dichloropyridine-2-carboxylic acid. Phenoxy acetic acid herbicides including 2,4-Dichlorophenoxy acetic acid (2,4-D) and 4-chloro-2-methylphenoxy acetic acid (MCPA) and their esters such as the 2-ethylhexyl and butoxy ethanol esters are used to control broadleaf weeds in crops such as cereals, sugar cane turf pastures and the like. Auxin herbicides are generally of formula

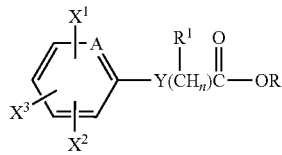

wherein
R is the alcohol portion of the ester or is a salt counter ion such a substituted ammonium counter ion;
A is nitrogen or CH;
$X^1$, $X^2$ and $X^3$ are independently selected from hydrogen, halogen (preferably chloro) and methyl, preferably from hydrogen and chloro and most preferably at least two of $X^1$, $X^2$ and $X^3$ are selected from chloro and methyl;
Y is a bond, oxygen or 1,4-oxyphenoxy;
$R^1$ is selected from hydrogen and methyl and preferably is hydrogen; and
n is from 0 to 3.
Dicamba is of formula:

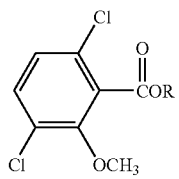

The amine salts of the auxin herbicides are in many cases water soluble and aqueous formulations of the amine salts are convenient to use. High concentrations of the amine salts can be prepared thereby potentially minimising the need to transport water in the formulated product while at the same time avoiding or minimising the need to use solvents with the potential disadvantages of flammability, and residue.

At the site of use the concentrate formulations can conveniently be diluted in a spray tank for soil or foliar application.

One of the significant limitations on the formulation and use of the auxin amine salts is the poor solution stability at low temperature particularly in highly concentrated solutions, for example of at least 500 g/L (based on active acid equivalent). This places limitations on the storage and handling of the auxin amine salts, including dicamba, with the result that the loading of salt needs to be lower than would normally be stable due to the propensity to form a significant proportion of crystalline deposits at low temperature which are not always readily redissolved.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY

We have found that the solution stability of dicamba may be significantly improved allowing significantly higher loadings to be formulated by using a combination of the monomethylamine (MMA) and dimethylamine (DMA) salts of dicamba. Accordingly we provide a herbicide composition comprising dicamba in the form of each of the monomethylamine and dimethyl amine salts. The molar ratio of dicamba in the monomethylamine:dimethylamine salts is preferably in the range of from 1:20 to 1:1 and more preferably 1:20 to 4:6. In one set of embodiments the ratio is from 1:20 to 3:7

We further provide a herbicide composition comprising dicamba in the form of the monomethylamine salt and dicamba in the form of the dimethylamine salt wherein the molar ratio of monomethylamine to dimethylamine is in the range of from 1:20 to 1:1 and preferably from 1:20 to 4:6.

In one set of embodiments the molar ratio of monomethylamine:dimethylamine comprises no lower proportion of monomethylamine salt than 1:15, more preferably 1:12 and more preferably 1:8. In one set of embodiments the ratio is from 4:6 to 1:1.

In an embodiment dicamba is in an aqueous composition and the concentration of dicamba in the aqueous composition is at least 500 g/L (preferably at least 600 g/L, more preferably at least 625 g/L, still more preferably 650 g/L and still more preferably at least 700 g/L) based on herbicidal acid equivalent.

In one embodiment there is provided a solid composition for forming the aqueous liquid herbicide composition on dilution with water the solid composition comprising dicamba in the form of the monomethylamine salt and dicamba in the form of the dimethylamine salt wherein the molar ratio of monomethylamine to dimethylamine is in the range of from 1:20 to 1:1 and preferably 1:20 to 4:6. In one embodiment the ratio is from 1:20 to 3:7. It is preferred that the molar ratio of monomethylamine:dimethylamine comprises no lower proportion of monomethylamine salt than 1:15, more preferably 1:12 and more preferably 1:8.

In another embodiment there is provided a process for preparing a composition described above comprising providing dicamba and reacting the acid form of dicamba with methylamine and dimethylamine in a molar ratio of from 1:20 to 1:1 and preferably from 1:20 to 4:6. In one set of embodiments the ratio is from 1:20 to 3:7. It is preferred that the molar ratio of monomethylamine:dimethylamine comprises no lower proportion of monomethylamine salt than 1:15, more preferably 1:12 and more preferably 1:8.

In another embodiment there is provided a method of preparing an aqueous liquid herbicide composition comprising dissolving an auxin monomethylamine salt and herbicidal dimethylamine salt of an auxin herbicide in an aqueous liquid to provide a composition as hereinbefore described.

Throughout the description and the claims of this specification the word "comprise" and variations of the word, such as "comprising" and "comprises" is not intended to exclude other additives, components, integers or steps.

DETAILED DESCRIPTION

While auxin herbicide salts are generally of formula:

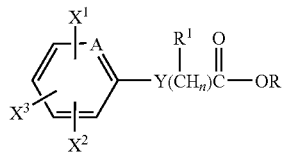

wherein
A is nitrogen or CH;
$X^1$, $X^2$ and $X^3$ are independently selected from hydrogen, halogen (preferably chloro) and methyl, preferably from hydrogen and chloro and most preferably at least two of $X^1$, $X^2$ and $X^3$ are selected from chloro and methyl;
Y is a bond, oxygen or 1,4-oxyphenoxy;
R is the monomethylamine or dimethylamine counter ion;
$R^1$ is selected from hydrogen and methyl and preferably is hydrogen; and
n is from 0 to 3;
the auxin herbicide component of the composition includes dicamba (3,6-dichloro-o-anisic acid).

The composition may if desired include other herbicides including other amine salts of auxins. In one set of embodiments the monomethylamine and dimethylamine constitute at least 80% by weight of the amine content of the composition, preferably at least 90% by weight of the amine content and most preferably at least 95% by weight of the amine content.

In a particularly preferred embodiment the concentration of dicamba herbicide is at least 500 g/L (preferably at least 600 g/L, more preferably at least 625 g/L, still more preferably 650 g/L and still more preferably at least 700 g/L) based on acid herbicidal acid equivalent.

The pH of the aqueous herbicide concentrate is preferably in the range of from 6 to 10.

The composition may be prepared by mixing of the dicamba amine salts in the prescribed ratio or alternatively one or both of the salts may be formed by reaction of monomethylamine and dimethylamine with the dicamba. Accordingly, in one embodiment there is provided a process for preparing a dicamba salt composition comprising providing dicamba in the form of the acid and reacting the acid with methylamine and dimethylamine in a molar ratio of 1:20 to 1:1 and preferably 1:20 to 4:6. It is preferred that the molar ratio of monomethylamine:dimethylamine comprises no lower proportion of monomethylamine than 1:15, more preferably 1:12 and more preferably 1:8.

In one embodiment there is provided a method of controlling plant growth comprising diluting a composition a concentrate composition as hereinbefore described with water and applying the diluted composition to plants or to soil in which growth of plants are to be controlled. The composition may, for example, be diluted with water to provide a concentration of dicamba herbicide salt in the range of from 0.1 g/L to 150 g/L (based on acid equivalent).

The dicamba salt concentrate composition may, for example, be applied at a rate of from 0.01 kg/ha to 5 kg/ha based on total acid equivalent in order to achieve control of weeds.

In some cases solvents have been used in concentrate auxin compositions such as ethylene glycol, in an attempt to limit the formation of crystalline deposits during storage of the aqueous liquid concentrate. The compositions of this invention may if desired be free of non-aqueous solvents such as ethylene glycol. Accordingly in one embodiment the herbicide composition comprising solution of dicamba herbicide in the form of the monomethylamine salt and dicamba herbicide in the form of the dimethylamine salt wherein the molar ratio of monomethylamine to dimethylamine is in the range of from 1:20 to 1:1 and preferably 1:20 to 4:6 and contains no more than 5% by weight non-aqueous solvents and more preferably is essentially free of non-aqueous solvents.

In a further embodiment the composition consists essentially of:
i) dicamba herbicide in the form of the monomethylamine salt and auxin herbicide in the form of the dimethylamine salt wherein the molar ratio of monomethylamine to dimethylamine is in the range of from 1:20 to 1:1 and preferably 1:20 to 4:6. It is preferred that the molar ratio of monomethylamine:dimethylamine comprises no lower proportion of monomethylamine salt than 1:15, more preferably 1:12 and more preferably 1:8;
ii) water;
iii) no more than 10% by weight, preferably no more than 5% and more preferably no more than 2% by weight based on the total weight of the composition of additives selected from surfactants and compatibility agents; and
iv) wherein the concentration of dicamba salt herbicide in the aqueous composition is at least 500 g/L (preferably at least 600 g/L, more preferably at least 625 g/L, still more preferably 650 g/L and still more preferably at least 700 g/L) based on acid herbicidal acid equivalent.

The composition of the invention may and preferably will include a compatibility agent such as casein or EDTA which we have found to improve compatibility of the auxin amine salts and other herbicides. The amount of compatibility agent may be at least a compatibility enhancing amount. In a preferred embodiment the composition according to the invention further comprising casein in an amount of from 0.05 to 10 parts by weight casein per 100 parts by weight auxin herbicide acid equivalent. The amount of casein is preferably from 0.01 to 5% by weight of a concentrate composition and more preferably is from 0.1 to 5% by weight of the composition.

Examples of surfactants include, nonaromatic-based surfactants, e.g. those based on heterocycles, olefins, aliphatics or cycloaliphatics, for example surface-active mono- or poly-alkyl-substituted and subsequently derivatized, e.g. alkoxylated, sulfated, sulfonated or phosphated, pyridine, pyrimidine, triazine, pyrole, pyrrolidine, furan, thiophene, benzoxazole, benzthiazole and triazole compounds, and/or aromatic-based surfactants, e.g. mono- or poly-alkyl-substituted and subsequently derivatized, e.g. alkoxylated, sulfated, sulfonated or phosphated, benzenes or phenols. The surfactants are generally soluble in the solvent phase and are preferably suitable for emulsifying it (together with active ingredients dissolved therein) upon dilution with water to give a spray liquor. The surfactant component when present in compositions according to the invention can, for example, comprise nonaromatic or aromatic surfactants or mixtures of nonaromatic and aromatic surfactants.

The mixed salt dicamba herbicide with the defined molar ratio of MMA:DMA exhibit an enhanced cold storage stability and reduced crystal growth at cold temperatures. The compositions also exhibit an improvement in stability in solution when diluted with water of variable quality that tends to produce precipitation in other auxins in concentrate compositions.

In one set of embodiments when the aqueous composition is subject to "cold storage testing" referred to herein (CIPA Method 39.3) (1999) it remains homogeneous with no more than 5% crystallization at 0° C. preferably no more than 2% and more preferably no more than 1% crystallization and most preferably no detectable crystallization. In the tests the composition remains homogeneous, clear and free of crystals at 0° C.

The invention will now be described with reference to the following examples. It is to be understood that the examples are provided by way of illustration of the invention and that they are in no way limiting to the scope of the invention.

EXAMPLES

In the drawings:

FIG. 1 is a graph showing the percent crystallisation of a Dicamba composition of 800 g/L ae as the percentage of MMA in a MMA/DMA mixture is increased from 0 to 100%.

Compositions described in the Examples were examined by the CIPAC Method 39.3 (1999) the procedure of which is noted below.

Procedure

Transfer 100±1.0 ml of the formulation to the tube and insert the stopper. Cool to 0±2° C. in the refrigerator (Note 2). If the sample contains a dissolved crystalline pesticide, remove the tube from the refrigerator after 24 hours, take off the stopper, add a small crystal of the pure or technical pesticide (Note 3) and replace the stopper. Replace the tube in the refrigerator and allow it to remain at 0±2° C. for a total period of 7 days (Note 4).

At the end of this time, note the volume and nature of any separated material. If the liquid phase is not homogeneous, note the volume of each layer. If there is any separated material, then allow the tube to reach room temperature over a period of 24 hours (Note 5), invert once and again note the volume and nature of any separated material.

Note 1 A domestic refrigerator is often unsuitable because the on/off cycle may cover a range larger than 4° C.

Note 2 Alternatively a graduated emulsion tube meeting BS 658 class B, type 1 (Crow Receiver) may be used.

Note 3 A crystal from the commercial manufacturing process is preferred. Alternatively a crystal separated from the formulation e.g. by distillation of the solvent may be used.

Note 4 Other temperature-storage period combinations may be specified.

Note 5 Room temperature being defined as 23±2° C. Note any temperature outside this range.

Example 1

This example compares the storage stability at 0° C. of compositions having a range of molar proportions of monomethylamine and dimethylamine salts prepared in accordance with Example 1 at a concentration of 650 g/L ae.

The composition of Example 1 was prepared with the exception that the ratio of monomethylamine (MMA) and dimethylamine (DMA) was varied.

Low temperature stability testing was carried out in accordance with the Standard CIPAC Method 39.3 (1999) and the resulting percentage crystallisation is reported in Table 3.

Examples 1 and 1a

The compositions of Examples 1 and 1a comprising DMA and MMA salts of Dicamba were prepared by mixing the components identified in the following Tables 1 and 1a in the amounts by weight specified.

TABLE 1

| Example 1 Ingredient | DICAMBA 800 g/L (ae) present as the DMA (80%) & MMA (20%). Weight (g) |
|---|---|
| Dicamba Technical (98%) | 853.8 |
| MMA (40%) | 62.4 |
| DMA (60%) | 249.8 |
| Compatibility agent | 4.0 |
| Water | To 1 L |

TABLE 1a

| Example 1a Ingredient | DICAMBA 800 g/L (ae) present as the DMA (70%) & MMA (30%) Weight (g) |
|---|---|
| Dicamba Technical (98%) | 853.8 |
| MMA (40%) | 93.7 |
| DMA (60%) | 218.6 |
| Compatibility agent | 4.0 |
| Water | To 1 L |

Example 2

The cold temperature crystallization in mixed salt compositions of Dicamba was determined for compositions of 700 g/L, 750 g/L and 800 g/L acid equivalent dicamba and the results are shown in Tables 2a, 2b and 2c. The percent crystallisation of DMA/MMA mixture with increasing percent MMA content for 800 g/L acid equivalent Dicamba formulations is shown on FIG. 1.

TABLE 2a

| Dicamba Formulation | 700 g/Lae MMA | DMA | % Crystallization at 0 deg. C. |
|---|---|---|---|
| Comparative 2a.1 | 0 | 100 | 0 |
| Comparative 2a.2 | 100 | 0 | 80 |

TABLE 2b

| Dicamba Formulation | 750 g/Lae MMA | DMA | % Crystallization at 0 deg. C. |
|---|---|---|---|
| Comparative 2b.1 | 0 | 100 | 2 |
| Composition Example 2b.2 | 10 | 90 | 1 |

TABLE 2b-continued

| Dicamba Formulation | 750 g/Lae MMA | DMA | % Crystallization at 0 deg. C. |
|---|---|---|---|
| Composition Example 2b.3 | 20 | 80 | 0 |
| Composition Example 2b.4 | 30 | 70 | 0 |
| Composition Example 2b.5 | 40 | 60 | 0 |

TABLE 2c

| Dicamba Formulation | 800 g/Lae MMA | DMA | % Crystallization at 0 deg. C. |
|---|---|---|---|
| Comparison 2c.1 | 0 | 100 | 10 |
| Composition Example 2c.2 | 10 | 90 | 5 |
| Composition Example 2c.3 | 20 | 80 | 1 |
| Composition Example 2c.4 | 30 | 70 | 0 |
| Comparison 2c.5 | 100 | 0 | 100 |
| Composition Example 2c.6 | 40 | 60 | 0 |

Example 3

The following compositions of the MMA:DMA mixed salts of dicamba were prepared and the stability at 0° C. and stability on dilution were determined.

(a) Dicamba at 800 g/L acid equivalent (ae).
   A composition of dicamba containing:
   60% DMA:40% MMA were prepared and found to be cold storage and dilution stable at the 800 g/L concentration.
   A dicamba composition was prepared containing:
   70% DMA:30% MMA mixture and was tested and found to have good low temperature stability and was stable on dilution.
   Neither of the individual DMA or MMA salts were stable at this concentration.

(b) 750 g/L Dicamba (based on acid equivalent)
   Mixtures of salts reported below were prepared and examined for cold temperature stability at 0° C. and stability on dilution.
   (i) A composition of dicamba 750 g/L (ae) as 60% DMA: 40% MMA salt mixture;
   (ii) 70% DMA:30% MMA;
   (iii) 80% DMA:20% MMA;
   (iv) 90% DMA:10% MMA;
   were each prepared and found to be stable at 0° C. and stable on dilution.
   Individual DMA and MMA salts were not stable at 750 g/L.

The invention claimed is:

1. A herbicidal composition comprising an aqueous solution of dicamba in each of the monomethylamine and dimethylamine salts wherein the molar ratio of monomethylamine: dimethylamine is from 1:20 to 4:6 and the concentration of dicamba herbicide is at least 500 g/L based on herbicide acid equivalent.

2. A herbicidal composition according to claim 1 wherein the molar ratio of monomethylamine to dimethylamine salts is in the range of from 1:15 to 4:6.

3. A herbicidal composition according to claim 2 wherein the monomethylamine and dimethylamine constitute at least 80% by weight of the amine content of the composition.

4. A herbicidal composition according to claim 3 wherein the monomethylamine and dimethylamine constitute at least 90% by weight of the amine content of the composition.

5. A herbicidal composition according to claim 3 wherein the monomethylamine and dimethylamine constitute at least 95% by weight of the amine content of the composition.

6. A herbicidal composition according to claim 1 wherein said molar ratio is from 1:12 to 3:7.

7. A herbicidal composition according to claim 1 wherein the concentration of dicamba herbicide is at least 600 g/L based on herbicide acid equivalent.

8. A herbicidal composition according to claim 1 wherein the concentration of dicamba herbicide is at least 650 g/L based on herbicide acid equivalent.

9. A herbicidal composition according to claim 1 wherein the concentration of dicamba herbicide is at least 700 g/L based on herbicide acid equivalent.

10. A solid composition comprising dicamba herbicide in the form of the monomethylamine salt and dicamba in the form of the dimethylamine salt wherein the molar ratio of monomethylamine to dimethylamine is in the range of from 1:20 to 4:6.

11. A solid composition according to claim 10 wherein the molar ratio of monomethylamine to dimethylamine is in the range of from 1:20 to 3:7.

12. A method of preparing an aqueous liquid herbicide composition according to claim 1, comprising dissolving dicamba monomethylamine salt and dicamba dimethylamine in an aqueous liquid, wherein the molar ratio of monomethylamine:dimethylamine is from 1:20 to 4:6 and the concentration of dicamba herbicide is at least 500 g/L based on herbicide acid equivalent.

13. A method for preparing an aqueous liquid herbicidal composition according to claim 1 comprising providing dicamba and reacting dicamba with methylamine and dimethylamine in a molar ratio of 1:20 to 4:6 in an aqueous liquid, wherein the concentration of dicamba herbicide is at least 500 g/L based on herbicide acid equivalent.

14. A method according to claim 13 wherein the molar ratio of monomethylamine:dimethylamine is from 1:12 to 3:7.

15. A method of controlling plant growth comprising diluting a composition according to claim 1 with water and applying the diluted composition to plants or to soil in which growth of plants is to be controlled.

16. A method according to claim 15 wherein the composition is diluted with water to provide a concentration of dicamba herbicide salt in the range of from 0.1 g/L to 150 g/L (based on acid equivalent).

17. A method according to claim 16 wherein the salt composition is applied at a rate of from 0.01 kg/ha to 2.5 kg/ha based on total acid equivalent.

* * * * *